(12) United States Patent
Wright

(10) Patent No.: US 6,668,382 B1
(45) Date of Patent: Dec. 30, 2003

(54) BABY GARMENT

(76) Inventor: Andre L. Wright, 14218 Hampshie Hall Ct., Upper Marlboro, MD (US) 20772

( * ) Notice: Subject to any disclaimer, the term of this patent is extended or adjusted under 35 U.S.C. 154(b) by 0 days.

(21) Appl. No.: 10/292,933

(22) Filed: Nov. 13, 2002

(51) Int. Cl.$^7$ .............................................. A41D 11/00
(52) U.S. Cl. ............................ 2/75; 2/69.5; 24/DIG. 41
(58) Field of Search ................................ 2/69, 69.5, 73, 2/75, 76, 78.2, 78.3, 78.4, 80, 83, 111, 113, 114, 235, 265, 104, 96, 128; D2/700, 709, 718, 719; 24/DIG. 41, 586.1, 586.11

(56) References Cited

U.S. PATENT DOCUMENTS

| 302,901 | A | * | 8/1884 | Fenne | 2/114 |
|---|---|---|---|---|---|
| 1,308,396 | A | * | 7/1919 | Chatfield | 2/78.2 |
| 1,393,468 | A | * | 10/1921 | Thayer | 2/78.2 |
| 1,432,804 | A | * | 10/1922 | Swantees | 2/78.2 |
| 1,439,502 | A | * | 12/1922 | Cahn | 2/80 |
| 1,512,171 | A | * | 10/1924 | Homling | 2/78.2 |
| 1,998,051 | A | * | 4/1935 | Gerber | 2/114 |
| 2,260,426 | A | * | 10/1941 | Bailey | 2/96 |
| 2,440,752 | A | * | 5/1948 | Mathews | 2/70 |
| 2,648,110 | A | * | 8/1953 | Baskind | 24/305 |
| 2,734,194 | A | * | 2/1956 | Colvin | 2/80 |
| 2,911,650 | A | * | 11/1959 | Gerich | 2/74 |
| 3,166,762 | A | * | 1/1965 | Winkworth | 2/80 |
| 3,840,900 | A | * | 10/1974 | Cruz | 2/77 |
| 3,979,802 | A | * | 9/1976 | Bongartz et al. | 24/630 |
| 4,663,782 | A | * | 5/1987 | Knox et al. | 2/104 |
| 4,688,270 | A | * | 8/1987 | Denicola et al. | 2/102 |
| 5,093,932 | A | * | 3/1992 | Doyle | 2/114 |
| 5,100,399 | A | * | 3/1992 | Janson et al. | 604/386 |
| 5,112,326 | A | * | 5/1992 | Quadrini | 604/391 |
| 5,440,763 | A | * | 8/1995 | Shah et al. | 2/114 |
| 5,564,126 | A | * | 10/1996 | Chou | 2/114 |
| 5,685,174 | A | * | 11/1997 | Balzer et al. | 63/29.1 |
| 5,926,845 | A | * | 7/1999 | Troyer | 2/93 |
| 5,946,722 | A | * | 9/1999 | Trautmann | 2/83 |
| 6,032,289 | A | * | 3/2000 | Villapiano | 2/102 |
| 6,216,270 | B1 | * | 4/2001 | Moquin et al. | 2/69 |
| 6,223,352 | B1 | * | 5/2001 | Watlington | 2/80 |
| 6,243,871 | B1 | * | 6/2001 | Fidler | 2/80 |
| 6,266,822 | B1 | * | 7/2001 | Joyce | 2/83 |
| 6,353,935 | B1 | * | 3/2002 | Antonini | 2/115 |
| 6,438,758 | B1 | * | 8/2002 | Burkard et al. | 2/115 |

* cited by examiner

Primary Examiner—John J. Calvert
Assistant Examiner—Alissa L. Hoey

(57) ABSTRACT

A baby garment for allowing the umbilical portion of a baby to be exposed to facilitate the healing thereof. The baby garment includes also including limb portions, and further having longitudinal edges extending lengthwise thereof and being fastenable to one another to close the piece of material upon a front side of a baby; and also includes fasteners including garment-closing fasteners being spacedly attached along the longitudinal edges of the piece of material, and also including umbilical-exposing fasteners being attached to the midsection of the torso portion.

5 Claims, 3 Drawing Sheets

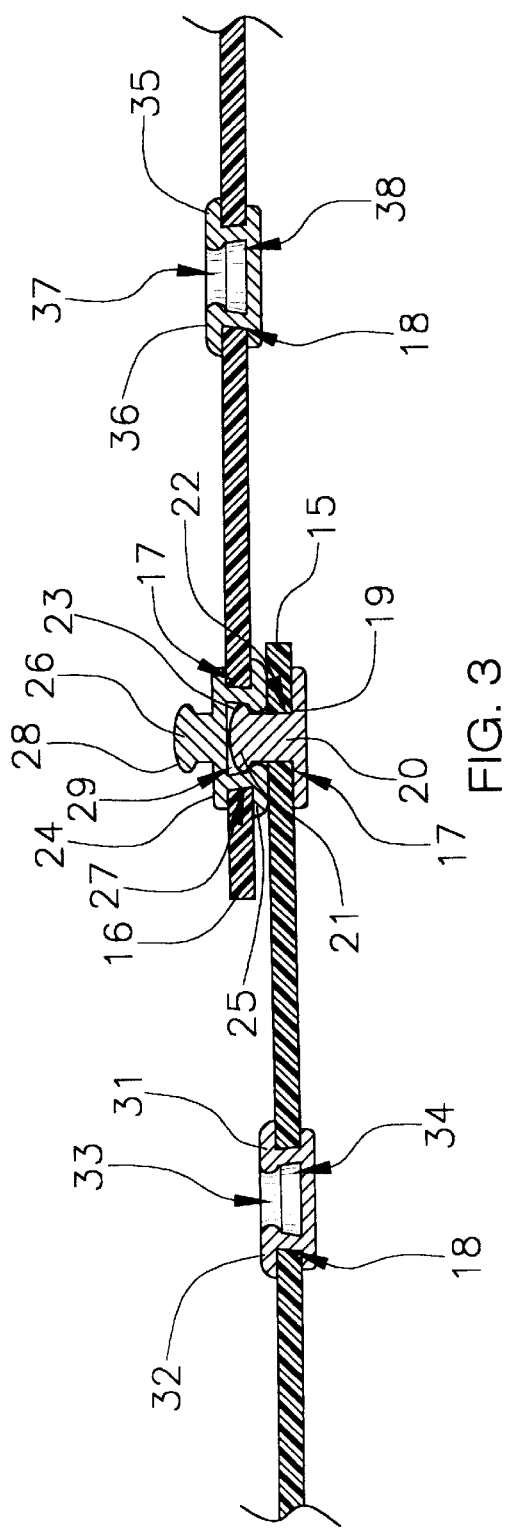
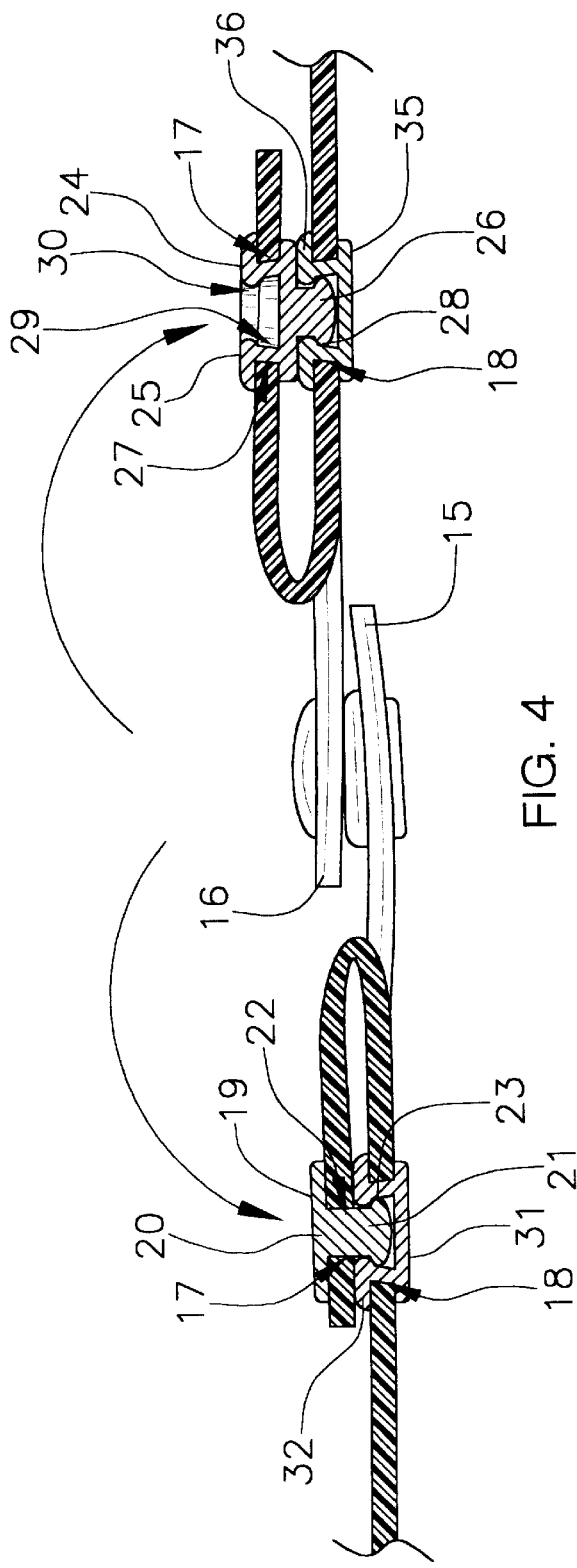
FIG. 3
FIG. 4

BABY GARMENT

BACKGROUND OF THE INVENTION

1. Field of the Invention

The present invention relates to umbilical-exposing garments and more particularly pertains to a new baby garment for allowing the umbilical portion of a baby to be exposed to facilitate the healing thereof.

2. Description of the Prior Art

The use of umbilical-exposing garments is known in the prior art. More specifically, umbilical-exposing garments heretofore devised and utilized are known to consist basically of familiar, expected and obvious structural configurations, notwithstanding the myriad of designs encompassed by the crowded prior art that have been developed for the fulfillment of countless objectives and requirements.

Known prior art includes U.S. Pat. No. 6,339,847; U.S. Pat. No. 1,125,467; U.S. Pat. No. 1,439,502; U.S. Pat. No. 2,622,248; U.S. Pat. No. Des. 188,893.

While these devices fulfill their respective, particular objectives and requirements, the aforementioned patents do not disclose a new baby garment. The prior art includes garments having fasteners from closing the garments about the users.

SUMMARY OF THE INVENTION

The general purpose of the present invention, which will be described subsequently in greater detail, is to provide a new baby garment which has many of the advantages of the umbilical-exposing garments mentioned heretofore and many novel features that result in a new baby garment which is not anticipated, rendered obvious, suggested, or even implied by any of the prior art umbilical-exposing garments, either alone or in any combination thereof. The present invention includes a piece of material including a torso portion having a midsection, and also including limb portions, and further having longitudinal edges extending lengthwise thereof and being fastenable to one another to close the piece of material upon a front side of a baby; and also includes fasteners including garment-closing fasteners being spacedly attached along the longitudinal edges of the piece of material, and also including umbilical-exposing fasteners being attached to the midsection of the torso portion. None of the prior art includes the combination of the elements of the present invention.

There has thus been outlined, rather broadly, the more important features of the baby garment in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new baby garment which has many of the advantages of the umbilical-exposing garments mentioned heretofore and many novel features that result in a new baby garment which is not anticipated, rendered obvious, suggested, or even implied by any of the prior art umbilical-exposing garments, either alone or in any combination thereof.

Still another object of the present invention is to provide a new baby garment for allowing the umbilical portion of a baby to be exposed to facilitate the healing thereof.

Still yet another object of the present invention is to provide a new baby garment that is easy and convenient to wear and use.

Even still another object of the present invention is to provide a new baby garment that prevents infections from setting in the umbilical region of the baby.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a partial cross-sectional view of the present invention.

FIG. 4 is another partial cross-sectional view of the present invention.

DESCRIPTION OF THE PREFERRED EMBODIMENT

Figure 1:
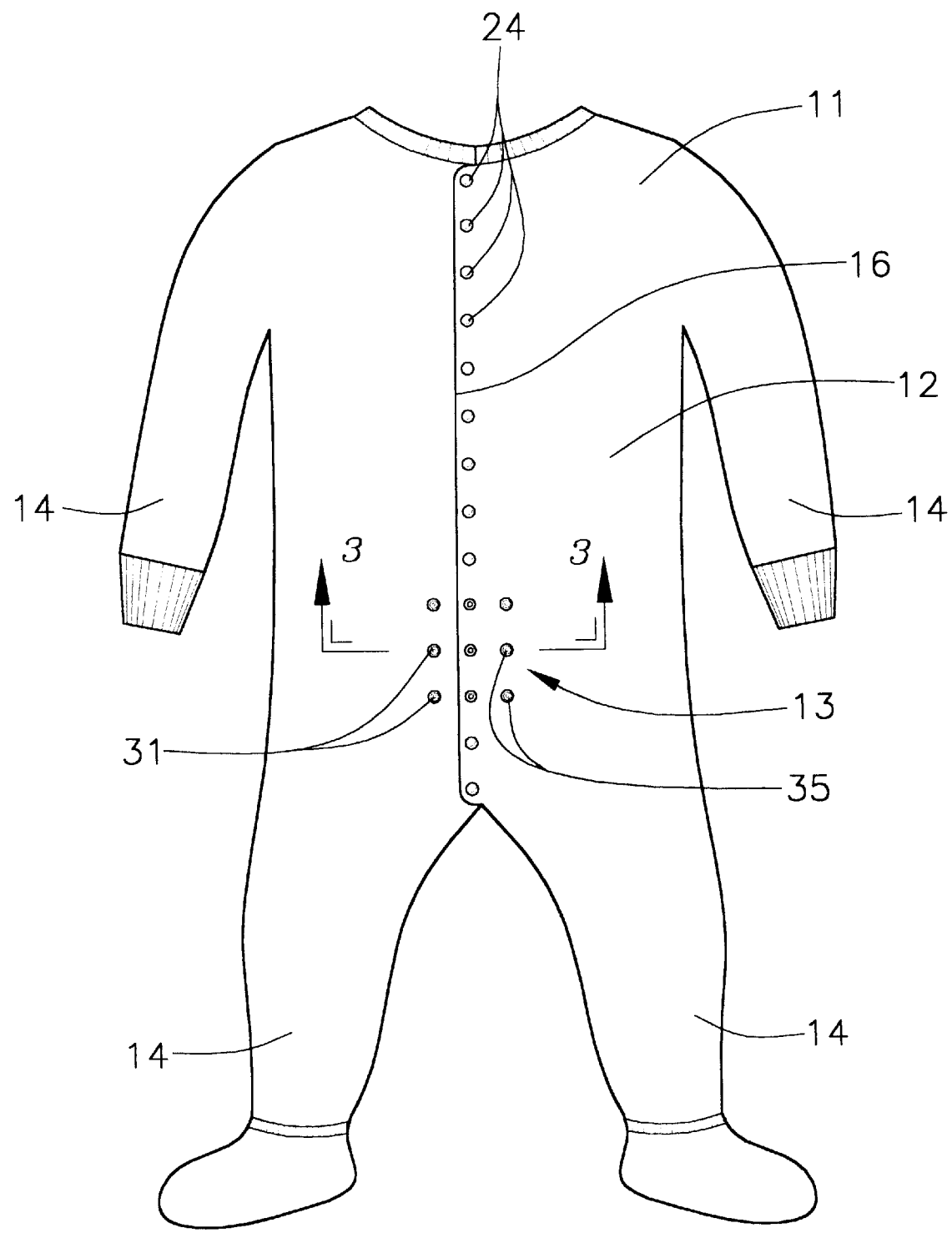
FIG. 1 is a front elevational view of a new baby garment according to the present invention.
Figure 2:
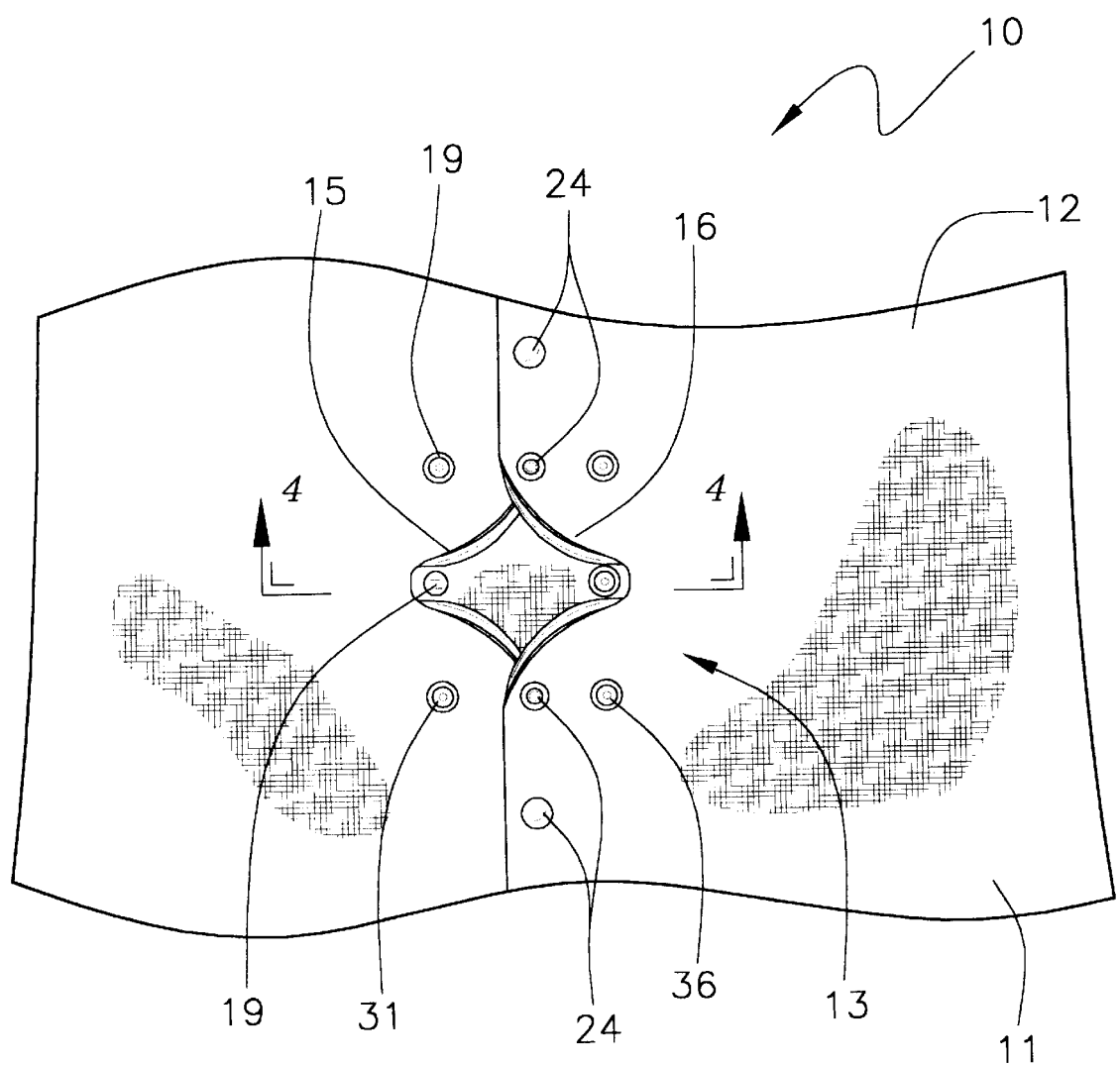
FIG. 2 is a detailed front elevational view of the present invention.

With reference now to the drawings, and in particular to FIGS. 1 through 4 thereof, a new baby garment embodying the principles and concepts of the present invention and generally designated by the reference numeral 10 will be described.

As best illustrated in FIGS. 1 through 4, the baby garment 10 generally comprises a piece of material 11 including a torso portion 12 having a midsection 13, and also including limb portions 14, and further having longitudinal edges 15,16 extending lengthwise thereof and being fastenable to one another to close the piece of material 11 upon a front side of a baby. The piece of material 11 also includes a plurality of holes 17,18 being spacedly disposed therethrough and along the longitudinal edges 15,16 and through the midsection 13 thereof.

Fasteners include garment-closing fasteners 19,24 being spacedly and conventionally attached along the longitudinal edges 15,16 of the piece of material 11, and also include umbilical-exposing fasteners 31,35 being conventionally attached to the midsection 13 of the torso portion 12. The garment-closing fasteners 19,24 include single fasteners 19 each having a base 20 and also having a nodule 21 being integrally attached to and extended from the base 20, and also includes dual fasteners 24 each having a base member 25 with a nodule-receiving slot 30 being disposed in one side thereof and also with a nodule member 26 being integrally attached to and extended from another side thereof. Each nodule 21 is removably engaged in the nodule-receiving slot 30 of a respective one of the dual fasteners 24 to close the piece of material 11 about the baby. The umbilical-exposing fasteners 31,35 include a first umbilical-exposing fastener 31 being spaced from one of the longitudinal edges 15 and being spaced from and aligned with and fastenable to one of the single fasteners 19, and also include a second umbilical-exposing fastener 35 being spaced from another of the longitudinal edges 16 and being spaced from and aligned with and fastenable to one of the dual fasteners 24 for removing a portion of the midsection 13 of the piece of material 11 to expose an umbilical region of the baby. Each of the umbilical-exposing fasteners 31,35 has a support portion 32,36 having a male-receiving slot 33,37 being disposed in a side thereof and also having an annular groove 34,38 being circumferentially disposed therein and engagably receiving an edge defining a respective one of the holes 18 of the piece of material 11. Each base 20 has an annular groove 22 being disposed in a circumferential edge thereof and engagably receiving an edge defining a respective one of the holes 17 of the piece of material 11, and each base member 25 has an annular groove 27 being disposed in a circumferential edge thereof and engagably receiving an edge defining a respective one of the holes 17 of the piece of material 11. Each of the nodules 21 and the nodule members 26 has an annular flange portion 23,28 being disposed about an outer end thereof. Each of the nodule-receiving slots 30 and the male-receiving slots 33,37 include an annular recessed portion 29 for receiving a respective annular flange portion 23,28.

In use, the user unfastens the single fastener 19 and the dual fastener 24 disposed upon the umbilical of the baby and fastens the single fastener 19 to the first umbilical-exposing fastener 31, and fastens the dual fastener 24 to the second umbilical-exposing fastener 35 to expose the umbilical of the baby so that air can facilitate healing of the umbilical.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the baby garment. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A baby garment comprising:

a piece of material including a torso portion having a midsection, and also including limb portions, and further having longitudinal edges extending lengthwise thereof and being fastenable to one another to close said piece of material upon a front side of a baby, said piece of material also including a plurality of holes being spaced disposed therethrough and along said longitudinal edges and through said midsection thereof; and fasteners including garment-closing fasteners being spacedly attached along said longitudinal edges of said piece of material, and also including umbilical-exposing fasteners being attached to said midsection of said torso portion, said garment-closing fasteners include single fasteners each having a base and also having a nodule being attached to and extended from said base, and also includes dual fasteners each having a base member with a nodule-receiving slot disposed in one side thereof and also with a nodule member being attached to and extended from another side thereof, each said nodule being removably engaged in said nodule-receiving slot of a respective one of said dual fasteners to close said piece of material about the baby, said umbilical-exposing fasteners including a first umbilical-exposing fastener being spaced from one of said longitudinal edges and being spaced from and aligned with and fastenable to one of said single fasteners, and also including a second umbilical-exposing fastener being spaced from another of said longitudinal edges and being spaced from and aligned with and fastenable to one of said dual fasteners for removing a portion of said midsection of said piece of material to expose an umbilical region of the baby.

2. A baby garment as described in claim 1, wherein each of said umbilical-exposing fasteners has a support portion having a male-receiving slot being disposed in a side thereof and also having an annular groove being circumferentially disposed therein and engageably receiving an edge defining a respective one of said holes of said piece of material.

3. A baby garment as described in claim 2, wherein each said base has an annular groove being disposed in a circumferential edge thereof and engageably receiving an edge defining a respective one of said holes of said piece of material, and each said base member has an annular groove being disposed in a circumferential edge thereof and engageably receiving an edge defining a respective one of said holes of said piece of material.

4. A baby garment as described in claim 3, wherein each of said nodules and said nodule members has an annular flange portion being disposed about an outer end thereof.

5. A baby garment as described in claim 4, wherein each of said nodule-receiving slots and said male-receiving slots include an annular recessed portion for receiving a respective said annular flange portion.

\* \* \* \* \*